United States Patent [19]

Kunz et al.

[11] 4,276,303
[45] Jun. 30, 1981

[54] MICROBICIDAL COMPOSITIONS

[75] Inventors: Walter Kunz, Oberwil; Wolfgang Eckhardt, Lörrach; Adolf Hübele, Magden, all of Switzerland

[73] Assignee: Ciba-Geigy Corporation, Ardsley, N.Y.

[21] Appl. No.: 174,412

[22] Filed: Aug. 1, 1980

Related U.S. Application Data

[62] Division of Ser. No. 6,398, Jan. 25, 1979, Pat. No. 4,233,308.

[30] Foreign Application Priority Data

Jan. 28, 1978 [CH] Switzerland .................. 931/78-7

[51] Int. Cl.³ .................. A01N 43/50; C07D 403/12
[52] U.S. Cl. .................. 424/273 R; 548/336
[58] Field of Search .................. 548/336; 424/273

[56] References Cited
U.S. PATENT DOCUMENTS

| | | | |
|---|---|---|---|
| 3,850,926 | 11/1974 | Stähle et al. | 548/336 |
| 4,046,911 | 9/1977 | Hubele | 424/285 |
| 4,061,722 | 12/1977 | Bodor | 548/336 |

Primary Examiner—Ethel G. Love
Attorney, Agent, or Firm—Frederick H. Rabin

[57] ABSTRACT

Acylated phenylaminotetrahydro-2-furanones of the formula

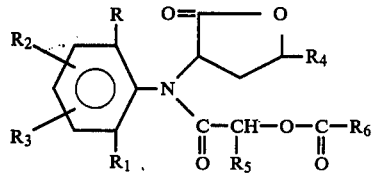

in which
R is $C_1$–$C_4$-alkyl, $C_1$–$C_4$-alkoxy or halogen,
$R_1$ is hydrogen, $C_1$–$C_3$-alkyl, $C_1$–$C_4$-alkoxy or halogen,
$R_2$ is hydrogen, $C_1$–$C_3$-alkyl or halogen,
$R_3$ is hydrogen or methyl, with the total number of C atoms of the substituents R, $R_1$, $R_2$ and $R_3$ in the phenyl ring not exceeding 8,
$R_4$ and $R_5$ independently of one another are hydrogen or methyl, and
$R_6$ is a $C_1$–$C_4$-alkyl group unsubstituted or substituted by halogen, thiocyano, cyano, $C_1$–$C_4$-alkoxy or $C_1$–$C_4$-alkylthio, or $R_6$ is a $C_2$–$C_5$-alkenyl or $C_3$–$C_7$-cycloalkyl group each unsubstituted or mono- or polysubstituted by halogen, or $R_6$ is a phenyl or benzyl group each unsubstituted or substituted by halogen, nitro, $C_1$–$C_4$-alkyl or $C_1$–$C_4$-alkoxy, or $R_6$ is a 5- or 6-membered heterocyclic radical unsubstituted or substituted by methyl, have a systemic action, are suggested as novel microbicides. They can be used in the form of pesticidal compositions in particular for combating phytopathogenic fungi, or for preventing fungus infections on cultivated plants.

6 Claims, No Drawings

MICROBICIDAL COMPOSITIONS

This is a divisional of application Ser. No. 006,398 filed on Jan. 25, 1979, now U.S. Pat. No. 4,233,308, issued Nov. 11, 1980.

The present invention relates to compounds of the formula I

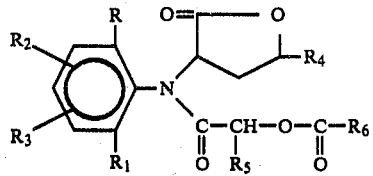

in which
R is $C_1$–$C_4$-alkyl, $C_1$–$C_4$-alkoxy or halogen,
$R_1$ is hydrogen, $C_1$–$C_3$-alkyl, $C_1$–$C_4$-alkoxy or halogen,
$R_2$ is hydrogen, $C_1$–$C_3$-alkyl or halogen,
$R_3$ is hydrogen or methyl, with the total number of C atoms of the substituents R, $R_1$, $R_2$ and $R_3$ in the phenyl ring not exceeding 8,
$R_4$ and $R_5$ independently of one another are hydrogen or methyl, and
$R_6$ is a $C_1$–$C_4$-alkyl group unsubstituted or substituted by halogen, thiocyano, cyano, $C_1$–$C_4$-alkoxy or $C_1$–$C_4$-alkylthio, or $R_6$ is a $C_2$–$C_5$-alkenyl or $C_3$–$C_7$-cycloalkyl group each unsubstituted or mono- or polysubstituted by halogen, or $R_6$ is a phenyl or benzyl group each unsubstituted or substituted by halogen, nitro, $C_1$–$C_4$-alkyl or $C_1$–$C_4$-alkoxy, or $R_6$ is a 5- or 6-membered heterocyclic radical unsubstituted or substituted by methyl,
to processes for producing these compounds, to compositions containing these compounds as active substances, and to the use of these active substances as microbicides for the protection of plants.

By alkyl or by alkyl moiety of an alkylthio or alkoxy group are meant, depending on the given number of carbon atoms, the following groups: methyl, ethyl, propyl, isopropyl, butyl, isobutyl, sec-butyl or tert-butyl. By alkenyl are meant in particular propenyl and vinyl. Halogen is fluorine, chlorine, bromine or iodine. A 5- or 6-membered heterocyclic radical contains one to three identical or different hetero atoms, and can be unsaturated, partially saturated or saturated. The following may be mentioned: thiophene, pyrrol, tetrahydrofuran, triazole, pyrazole, imidazole, pyridine, pyrimidine, pyrazine, pyridazine, morpholine or thiomorpholine. Tetrahydrofuran is preferred.

In the U.S. Pat. No. 3,933,860 are described 3-[N-acyl-N-arylamino]-lactones and -lactams as fungicides, which are derived from the structure of benzoyl-, alkanoyl or haloalkanoyl-(particularly haloacetyl-) anilides. Anilides of this type are described in the literature in very great numbers as herbicides, for example in U.S. Pat. Nos. 3,403,994, 3,442,945, 3,547,620, 3,637,847, 3,598,859 or 3,946,045.

It is therefore not surprising that the compounds mentioned in the U.S. Pat. No. 3,933,860 give rise in some cases, with the applied amounts necessary in practice, to undesirable phytotoxicity in the plants to be protected against fungus infection.

It has now been found that compounds with the structure of the formula I surprisingly exhibit a very favourable microbicidal spectrum for practical requirements for the protection of cultivated plants, without affecting these disadvantageously by producing undesired secondary effects. Cultivated plants within the scope of the present invention are for example cereals, maize, rice, vegetables, sugar beet, soya bean, groundnuts, fruit trees or ornamental plants, especially however grape vines, hops, cucumber plants (cucumbers, pumpkins, melons), solanaceae, such as potatoes, tobacco and tomatoes, and also bananas, cocoa and natural rubber plants.

Fungi occurring on plants or on parts of plants (fruit, blossom, foliage, stalks, tubers or roots) of the said crops and of related cultivated crops can be inhibited or destroyed with the active substances of the formula I, and also parts of plants subsequently growing remain preserved from such fungi. The active substances are effective against the phytopathogenic fungi belonging to the following classes: Ascomycetes (e.g. Erysiphaceae); Basidiomycetes, such as in particular rust fungi; Fungi imperfecti (e.g. Moniliales); and especially against the Oomycetes belonging to the Phycomycetes class, such as Phytophthora, Peronospora, Pseudoperonospora, Pythium or Plasmopara. Furthermore, the compounds of the formula I have a systemic action. They can also be used as dressing agents for the treatment of seed (fruits, tubers and grain) and plant cuttings to protect them from fungus infections, and also against phytopathogenic fungi occurring in the soil.

Compounds of the formula I preferred as plant fungicides are those in which R is methyl, $R_1$ is methyl, ethyl or chlorine, $R_2$ is hydrogen, halogen or methyl, and $R_3$ is hydrogen or methyl, and $R_4$, $R_5$ and $R_6$ are as defined under the formula I. This group is to be called compound group Ia.

Among these compounds of the group Ia, is to be emphasised, as one of the important subgroups, the group in which $R_4$ and $R_5$ are hydrogen or methyl, and $R_6$ is methyl, vinyl, methoxymethyl or tetrahydrofuranyl. This is to be called compound group Ib.

A further important subgroup within the compound group Ia is that in which $R_4$ and $R_5$ are hydrogen or methyl, and $R_6$ is a five-membered ring having 2 or 3 nitrogen atoms. This is to be called compound group Ic.

Important individual compounds are for example:
3-[N-(acetoxyacetyl)-N-(2,3,6-trimethylphenyl)]-amino-tetrahydro-2-furanone,
3-[N-(acetoxyacetyl)-N-(2,6-dimethyl-3-chlorophenyl)]-amino-tetrahydro-2-furanone,
3-[N-(acetoxyacetyl)-N-(2,3,5,6-tetramethyl-phenyl)]-amino-tetrahydro-2-furanone,
3-[N-(tetrahydrofuranyloxyacetyl)-N-(2,6-dimethylphenyl)]-amino-tetrahydro-2-furanone, and
3-[N-(tetrahydrofuranyloxyacetyl)-N-(2,3,6-trimethylphenyl)]-amino-tetrahydro-2-furanone.

The compounds of the formula I are produced according to the invention
(A) by acylation of a compound of the formula II

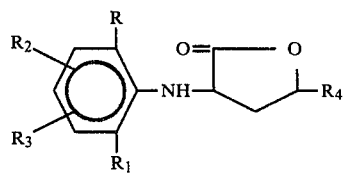

with a compound of the formula III

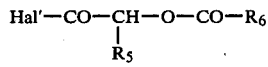 (III); or (B) by initial monohaloacylation of a compound of the formula II to a compound of the formula IV

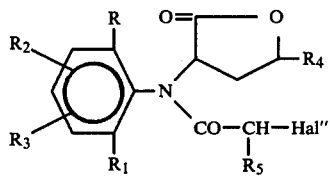 (IV), and exchange of the halogen atom Hal" for the acid radical of an acid HOCO—R$_6$ with the aid of the acid itself or of one of its salts, preferably the alkali metal or alkalineearth metal salt thereof; or (C) by reaction of a hydroxyacetanilide or of an α-hydroxypropionanilide of the formula V

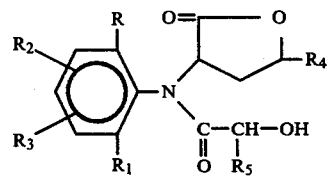 (V), in the presence of a mild base, with an acid halide Hal—CO—R$_6$; or (D), for obtaining derivatives of the formula I in which an N-containing heterocycle R$_6$ is bound by way of a nitrogen atom to the radical of the molecule, by reaction of the intermediate of the formula V with a corresponding compound of the formula VI

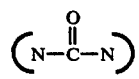 (VI)

in which the left and right halves are to represent the heterocycle to be introduced (for example imidazole, 1,2,4-triazole or pyrazole), in an aprotic nonpolar solvent.

In the formulae II, III, IV, V and VI, R to R$_6$ are as defined under the formula I, whilst Hal, Hal' and Hal" denote halogen, preferably chlorine or bromine.

The reactions can be performed in the presence or absence of solvents or diluents inert to the reactants. The following are for example suitable: aliphatic or aromatic hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethylformamide; dimethylsulfoxide, ketones such as methyl ethyl ketone; and mixtures of solvents of this kind.

For monohaloacetylation according to variant B, it is possible to use the corresponding carboxylic acids themselves and also esters thereof, advantageously however the acid anhydrides or the acid halides. The preferred acid halides in the variants B and C are the acid chlorides or acid bromides.

The reaction temperatures are between 0° and 120° C., preferably between 0° and 50° C. The use of acid-binding agents and condensation agents is in some cases advantageous. Suitable as such are tertiary amines such as trialkylamines (for example triethylamine), pyridine and pyridine bases, or inorganic bases, such as the oxides and hydroxides, hydrogen carbonates and carbonates of alkali metals and alkaline-earth metals, and also sodium acetate.

The production process A starting with compounds of the formula II and also the acylation step leading to compounds of the formulae IV and V can also be performed without acid-binding agents, and then it is advisable in some cases to pass nitrogen through to expel the formed hydrogen halide. In other cases, an addition of dimethylformamide as reaction catalyst is very advantageous.

Details regarding the production of intermediates of the formula II are known from the U.S. Pat. No. 3,933,860.

The compounds of the formula I possess in the lactone radical

an asymmetric centre (*) and in the case where R$_4$ is CH$_3$ a second asymmetric centre (**), and can be split in the customary manner (for example by fractional crystallisation or chromatographical separation) into optical antipodes, which have different strengths of microbicidal action.

If no specific synthesis has been performed for the isolation of pure isomers of the formula I, or of the employed butyrolactone, a product is usually obtained as an isomeric mixture.

The following Examples serve to further illustrate the invention without limiting its scope. The temperature values relate to degrees Centigrade.

EXAMPLE 1

Production of 3-[N-(acetoxyacetyl)-N-(2,3,6-trimethylphenyl)]-amino-tetrahydro-2-furanone

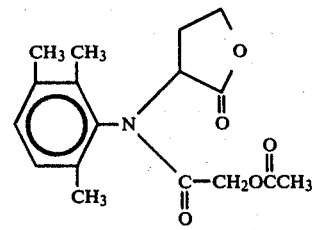

59.1 g of 3-[N-(chloroacetyl)-N-(2,3,6-trimethylphenyl)]-amino-tetrahydro-2-furanone is heated with 37.7 g of sodium acetate in 150 ml of absolute dimethylformamide for 48 hours at 110°. The reaction mixture is then cooled, poured into ice-water, taken up in methylene chloride and separated. The aqueous phase is extracted three times with methylene chloride, the combined extracts are washed three times with water, dried over sodium sulfate and concentrated by evaporation. The last traces of dimethylformamide are then removed at 90° under high vacuum, and ether and petroleum ether are added to the brown oil obtained, whereupon crystallisation occurs. Recrystallised from isopropanol with the aid of active charcoal, the product obtained as a diasterioisomeric mixture melts at 100°–102°.

In the manner described in Example 1, or by one of the processes described in the foregoing, there are obtained the following compounds:

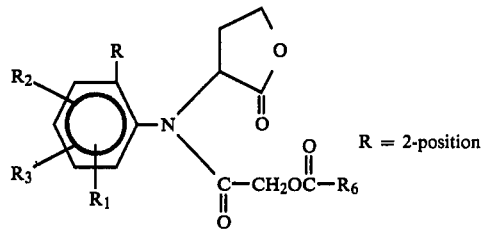

R = 2-position

TABLE I

| Comp. No. | R | $R_1$ | $R_2$ | $R_3$ | $R_6$ | Physical constants |
|---|---|---|---|---|---|---|
| 1 | $CH_3$ | 6-$CH_3$ | H | H | $CH_3$— | m.p. 82–84° |
| 2 | $CH_3$ | 6-$CH_3$ | H | H | $ClCH_2$— | m.p. 53–57° |
| 3 | $CH_3$ | 6-$CH_3$ | H | H | $CH_3OCH_2$— | m.p. 90–93° |
| 4 | $CH_3$ | 6-$CH_3$ | H | H | (tetrahydrofuryl) | m.p. 127–129° |
| 5 | $CH_3$ | 6-$CH_3$ | 3-$CH_3$ | 5-$CH_3$ | $CH_3$— | m.p. 171–173° |
| 6 | $CH_3$ | 6-$CH_3$ | 3-$CH_3$ | H | (tetrahydrofuryl) | m.p. 91–108° |
| 7 | $CH_3$ | 6-$CH_3$ | 3-Cl | H | $CH_3$ | m.p. 88–95° |
| 8 | $CH_3$ | 6-$CH_3$ | H | H | $CH_3CH=CH$— | m.p. 121–122° |
| 9 | $CH_3$ | 6-$CH_3$ | H | H | (furyl) | m.p. 180–182° |
| 10 | $CH_3$ | 6-$CH_3$ | 3-$CH_3$ | H | $CH_3$— | m.p. 100–102° |
| 11 | $CH_3$ | 6-$C_2H_5$ | H | H | $CH_3$— | m.p. 73–75° |
| 12 | $CH_3$ | 6-$CH_3$ | 4-Cl | H | $CH_3$— | m.p. 96–98° |
| 13 | $CH_3$ | 6-$CH_3$ | 3-$CH_3$ | 5-$CH_3$ | $CH_3OCH_2$— | oil |
| 14 | $CH_3$ | 6-Cl | H | H | $CH_3$ | m.p. 74–76° |
| 15 | $CH_3$ | 6-$CH_3$ | H | H | $C_2H_5OCH_2$— | m.p. 95–98° |
| 16 | $CH_3$ | 6-$CH_3$ | H | H | Cl—(phenyl)— | |
| 17 | $CH_3$ | 6-$OCH_3$ | H | H | $CH_3$— | m.p. 159–160° |
| 18 | $CH_3$ | 6-$CH_3$ | 3-$CH_3$ | H | (cyclopropyl) | m.p. 102–106° |
| 19 | $CH_3$ | 6-$CH_3$ | 3-Cl | H | $NCS$—$CH_2$— | m.p. 58–63° |
| 20 | $CH_3$ | 6-$CH_3$ | H | H | (phenyl)—$CH_2$— | |
| 21 | $CH_3$ | 6-$CH_3$ | 3-$CH_3$ | H | $ClCH_2CH_2$— | m.p. 92–95° |
| 22 | $CH_3$ | 6-$CH_3$ | 3-$CH_3$ | 5-$CH_3$ | $CH_3CH_2$— | m.p. 175–178° |
| 23 | $CH_3$ | 6-$CH_3$ | H | H | $CH_3OCH_2CH_2$— | m.p. 94–98° |
| 24 | $CH_3$ | 6-$CH_3$ | H | H | $(CH_3)_2CH$— | m.p. 88–91° |
| 25 | $CH_3$ | 6-$CH_3$ | 3-$CH_3$ | H | (cyclohexyl-H)— | |
| 26 | $CH_3$ | 6-$CH_3$ | 3-$CH_3$ | 5-$CH_3$ | (tetrahydrofuryl) | m.p. 142–143° |
| 27 | $CH_3$ | 6-$CH_3$ | 3-$CH_3$ | H | $CH_3SCH_2$— | viscous |
| 28 | $CH_3$ | 6-$CH_3$ | H | H | $CH_3(CH_2)_3$— | m.p. 179–183° |
| 29 | $CH_3$ | 6-$CH_3$ | H | H | $HCCl=CCl$— | m.p. 161–165° |
| 30 | $CH_3$ | 6-$CH_3$ | H | H | (imidazolyl) | m.p. 137–140° |
| 31 | $CH_3$ | 6-$CH_3$ | H | H | $C_2H_5$ | m.p. 63–74° |
| 32 | $CH_3$ | 6-$CH_3$ | 3-$CH_3$ | H | (imidazolyl) | m.p. 191–94° | and also the following compounds of the formula

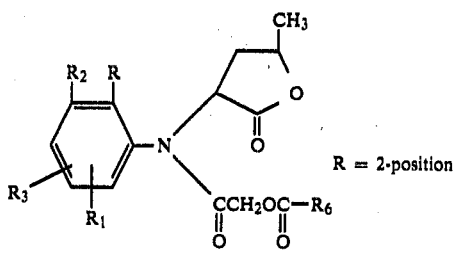

R = 2-position

TABLE II

| Comp. No. | R | $R_1$ | $R_2$ | $R_3$ | $R_6$ | Physical constants |
|---|---|---|---|---|---|---|
| 33 | $CH_3$ | 6-$CH_3$ | H | H | $CH_3$— | m.p. 132-135° |
| 34 | $CH_3$ | 6-$CH_3$ | 3-$CH_3$ | 5-$CH_3$ | $CH_3$— | m.p. 170-174° |
| 35 | $CH_3$ | 6-$CH_3$ | H | H | ⟨furyl⟩ | m.p. 172-176° |
| 36 | $CH_3$ | 6-$CH_3$ | H | H | $CH_3OCH_2$— | m.p. 102-104° |
| 37 | $CH_3$ | 6-$CH_3$ | H | H | $C_2H_5$— | m.p. 137-140° |
| 38 | $CH_3$ | 6-$CH_3$ | 3-Cl | H | $CH_3$ | m.p. 140-143° |
| 39 | $CH_3$ | 6-Cl | H | H | $CH_3$ | m.p. 116-120° |
| 40 | $CH_3$ | 6-$CH_3$ | H | H | $CH_3SCH_2$— | viscous |
| 41 | $CH_3$ | 6-$CH_3$ | 3-$CH_3$ | H | ⟨furyl⟩ | m.p. 138-142° |
| 42 | $CH_3$ | 6-$CH_3$ | H | H | $CH_3OCH_2CH_2$— | m.p. 96-99° |

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations: dusts and scattering agents (up to 10%), granulates [coated granules, impregnated granules and homogeneous granules] (1 to 80%);

liquid preparations:
(a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
(b) solutions (0.1 to 20%).

The active substances of the formula I of the present invention can be formulated for example as follows.

Dust:

The following substances are used to produce (a) a 5% dust and (b) a 2% dust:
(a)
   5 parts of active substance, and
   95 parts of talcum,
(b)
   2 parts of active substance,
   1 part of highly dispersed silicic acid, and
   97 parts of talcum.
The active substances are mixed and ground with the carriers, and in this form they can be applied by dusting.

Granulate:

The following substances are used to produce a 5% granulate:
   5 parts of active substance,
   0.25 part of epichlorohydrin,
   0.25 part of cetyl polyglycol ether,
   3.50 parts of polyethylene glycol, and
   91 parts of kaolin (particle size 0.3-0.8 mm).

The active substance is mixed with epichlorohydrin and dissolved in 6 parts of acetone, and the polyethylene glycol and cetyl polyglycol ether are then added. The solution obtained is sprayed onto kaolin, and the acetone is evaporated off in vacuo. A microgranulate of this kind is particularly suitable for soil application.

Wettable powder:

The following constituents are used to produce (a) a 70% wettable powder, (b) a 40% wettable powder, (c) and (d) a 25% wettable powder, and (e) a 10% wettable powder:

(a)
   70 parts of active substance,
   5 parts of sodium dibutylnaphthylsulfonate,
   3 parts of naphthalenesulfonic acid/phenolsulfonic acid/formaldehyde condensate 3:2:1,
   10 parts of kaolin, and
   12 parts of Champagne chalk;

(b)
   40 parts of active substance,
   5 parts of sodium lignin sulfonate,
   1 part of sodium dibutylnaphthalenesulfonate,
   54 parts of silicic acid;

(c)
   25 parts of active substance,
   4.5 parts of calcium lignin sulfonate,
   1.9 parts of Champagne chalk/hydroxyethyl cellulose mixture (1:1),
   1.5 parts of sodium dibutylnaphthalenesulfonate,
   19.5 parts of silicic acid,
   19.5 parts of Champagne chalk, and
   28.1 parts of kaolin;

(d)
   25 parts of active substance,
   2.5 parts of isooctylphenoxy-polyoxyethyleneethanol,
   1.7 parts of Champagne chalk/hydroxyethylcellulose mixture (1:1),
   8.3 parts of sodium aluminium silicate, 16.5 parts of kieselgur, and
46 parts of kaolin, and (e)
10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, and which can be diluted with water to give suspensions of the desired concentration, and these are particularly suitable for leaf application.

Emulsifiable concentrate:

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the desired concentration can be prepared from these concentrates by dilution with water, and they are particularly suitable for leaf application.

In order to widen their sphere of action and to adapt them to given circumstances, the compounds of the formula I can be used together with other suitable pesticides, for example fungicides, insecticides, acaricides, nematocides, rodenticides or herbicides, or with active substances influencing the growth of plants, and also with fertilisers.

EXAMPLE 2

Action against Phytophthora infestans on tomatoes (Ia) Residual-preventive action Tomato plants of the "Roter Gnom" (red gnome) variety are sprayed after three weeks' cultivation with a liquor containing 0.06% of active substance (prepared from the active substance made up as a wettable powder); the applied coating is allowed to dry, and the plants are then infested with a zoospore suspension of *Phytophthora infestans*. The plants subsequently remain for 6 days in a controlled-atmosphere chamber at 18° to 20°, with high atmospheric humidity produced by means of an artificial spray. Typical leaf spots appear after this length of time, and their size and number serve as a criterion for evaluation of the examined substance.

(Ib) Curative action

Tomato plants of the "Roter Gnom" variety are sprayed, after three weeks' cultivation, with a zoospore suspension of the fungus, and incubated in a chamber at 18° to 20° with saturated atmospheric humidity. The moistening treatment is interrupted after 24 hours; the plants are dried and then sprayed with a liquor containing the active substance formulated as a wettable powder, at a concentration of 0.06%. The applied coating is allowed to dry, and the plants are then returned to the moist-atmosphere chamber for 4 days. The number and size of the typical leaf spots appearing after this time serve as a criterion for an assessment of the effectiveness of the substances tested.

(II) Preventive-systemic action

The active substance in the form of a wettable powder is applied at a concentration of 0.006% (relative to the volume of soil) to the surface of the soil of three-week old potted tomato plants of the "Red Gnom" variety. After a period of three days, the underside of the leaves of the plants is sprayed with a zoospore suspension of Phytophthora infestans. The plants are then stored for 5 days in a spray chamber at 18°-20° with a saturated atmosphere. The typical leaf spots appear after this time; on the basis of their number and size, an evaluation is then made of the effectiveness of the substances tested.

In these three tests, the compounds of the formula I exhibit a good leaf-fungicidal action. The compounds Nos. 1, 7, 8, 9, 10, 38 and others prevent fungus infection completely. The compounds Nos. 7, 10 and 38 in the residual test prevent fungus infection even with a concentration of active substance of only 0.02%.

EXAMPLE 3

Action against *Plasmopara viticola* (Bert. et Curt.) (Berl. et DeToni) on grape vines Residual-preventive action Grape-vine cuttings of the "Chasselas" variety are grown in a greenhouse. Three plants are sprayed in the 10-leaf stage with a liquor prepared from the active substance formulated as a wettable powder (0.02% of active substance). After drying of the applied coating, the plants are uniformly infested on the underside of the leaves with the spore suspension of the fungus. The plants are subsequently kept for 8 days in a moist chamber. Clear symtoms of infection have appeared on the control plants after this period of time. The number and size of the areas of infection on the treated plants serve as a criterion for the evaluation of the effectiveness of the substances tested.

The compounds of the formula I have a good leaf-fungicidal action in this test. The grape-vine plants have a healthy appearance. The compounds Nos. 1, 7, 9, 10, 38 and others prevent fungus infection completely.

EXAMPLE 4

Action against Pythium debaryanum on *Beta vulgaris* (sugar beet)

(a) Action after soil application

The fungus is cultivated on sterile oat grains, and then applied to a soil/sand mixture. The soil infected in this manner is put into flower pots and sown with sugar-beet seeds. Directly after sowing, the test preparations (formulated as wettable powders) are poured as aqueous suspensions over the soil (20 ppm of active substance relative to the volume of soil). The pots are then kept for 2-3 weeks at 20°-24° in a greenhouse. The soil is maintained uniformly moist during this period by a light spraying with water. In the assessment of the test results, an observation is made of the emergence of the sugar-beet plants and also of the proportion of healthy and diseased plants, respectively.

(b) Action after dressing application

The fungus is cultivated on sterile oat grains and then applied to a soil/sand mixture. The soil infected in this manner is placed into flower pots and sown with sugar-beet seeds which have been dressed with the test preparations formulated as dressing powders (1000 ppm of active substance relative to the weight of seed). The sown pots are kept for 2-3 weeks at 20°-24° in a greenhouse. The soil during this period is maintained uniformly moist by a light spraying with water. In the assessment of the test results, the emergence of the sugar-beet plants is observed and the proportion of healthy and diseased plants, respectively, is determined. After the treatment with the active substances of the formula I, more than 80% of the sugar-beet plants emerge both under the test conditions (a) and (b), and the plants have a healthy appearance. Where treatment is carried out with compound No. 10, 93% of the plants emerge.

EXAMPLE 5

Action against *Cercospora personata* (=*C. arachidicola*) on groundnut plants

Three-week old groundnut plants are sprayed with a spray liquor produced from wettable powder of the active substance (0.02% of active substance). The treated plants are dusted after about 12 hours with a conidiospore suspension of the fungus. The infected plants are then incubated for about 24 hours with >90% relative humidity, and are subsequently transferred to a greenhouse at about 22°. The fungus infection is assessed after 12 days.

In comparison with the untreated control plants, plants which have been treated with active substances of the formula I display only slight fungus infection or virtually no infection at all. Fungus infection is completely prevented with the compounds Nos. 4, 7, 10 and 38.

What is claimed is:

1. A compound of the formula I

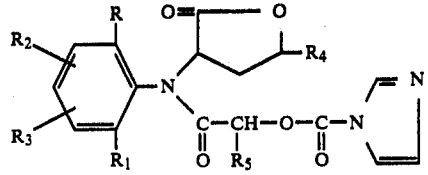

in which
R is $C_1$-$C_4$-alkyl, $C_1$-$C_4$-alkoxy or halogen,
$R_1$ is hydrogen, $C_1$-$C_3$-alkyl, $C_1$-$C_4$-alkoxy or halogen,
$R_2$ is hydrogen, $C_1$-$C_3$-alkyl or halogen,
$R_3$ is hydrogen or methyl, with the total number of C atoms of the substituents R, $R_1$, $R_2$ and $R_3$ in the phenyl ring not exceeding 8,
$R_4$ and $R_5$ independently of one another are hydrogen or methyl.

2. A compound of the formula I according to claim 1 in which R is methyl, $R_1$ is methyl, ethyl or chlorine, $R_2$ is hydrogen, halogen or methyl, and $R_3$ is hydrogen or methyl.

3. A compound according to claim 2 in which: R and $R_1$ are methyl; and $R_2$, $R_3$, $R_4$ and $R_5$ are hydrogen.

4. A compound according to claim 2 in which: R and $R_1$ are methyl; $R_2$ is methyl in the 3-position; and $R_3$, $R_4$ and $R_5$ are hydrogen.

5. A phytomicrobicidal composition which comprises as active ingredient an effective phytomicrobicidal amount of a compound of the formula I according to claim 1, together with a suitable carrier therefor.

6. A method for controlling phytopathogenic fungi, which comprises applying to plants or to a locus likely to be infected by such fungi a fungicidally effective amount of a compound according to claims 1, 2, 3 or 4.

* * * * *